(12) United States Patent
Tour et al.

(10) Patent No.: US 8,784,866 B2
(45) Date of Patent: Jul. 22, 2014

(54) WATER-SOLUBLE CARBON NANOTUBE COMPOSITIONS FOR DRUG DELIVERY AND MEDICINAL APPLICATIONS

(75) Inventors: James M. Tour, Bellaire, TX (US); Rebecca Lucente-Schultz, Houston, TX (US); Ashley Leonard, Houston, TX (US); Dmitry V. Kosynkin, Houston, TX (US); Brandi Katherine Price, Houston, TX (US); Jared L. Hudson, Hamilton, VA (US); Jodie L. Conyers, Jr., Houston, TX (US); Valerie C. Moore, Houston, TX (US); S. Ward Casscells, Houston, TX (US); Jeffrey N. Myers, Houston, TX (US); Zvonimir L. Milas, Houston, TX (US); Kathy A. Mason, Houston, TX (US); Luka Milas, Houston, TX (US)

(73) Assignees: William Marsh Rice University, Houston, TX (US); Board of Regents, The University of Texas System, Austin, TX (US)

( * ) Notice: Subject to any disclaimer, the term of this patent is extended or adjusted under 35 U.S.C. 154(b) by 894 days.

(21) Appl. No.: 12/245,438

(22) Filed: Oct. 3, 2008

(65) Prior Publication Data

US 2009/0170768 A1 Jul. 2, 2009

Related U.S. Application Data

(63) Continuation-in-part of application No. PCT/US2008/058268, filed on Mar. 26, 2008.

(60) Provisional application No. 60/908,115, filed on Mar. 26, 2007, provisional application No. 60/977,311, filed on Oct. 3, 2007.

(51) Int. Cl.
*A61F 2/00* (2006.01)
(52) U.S. Cl.
USPC ............. 424/424; 424/78.08; 424/78.17; 977/773
(58) Field of Classification Search
None
See application file for complete search history.

(56) References Cited

U.S. PATENT DOCUMENTS

| 5,473,055 | A | 12/1995 | Mongelli et al. | |
|---|---|---|---|---|
| 2004/0076681 | A1* | 4/2004 | Dennis et al. | 424/489 |
| 2005/0191680 | A1 | 9/2005 | Bruno et al. | |
| 2009/0036549 | A1 | 2/2009 | Yuge et al. | |
| 2010/0215724 | A1* | 8/2010 | Prakash et al. | 424/450 |

FOREIGN PATENT DOCUMENTS

| EP | 0932399 | 1/2006 |
|---|---|---|
| WO | 2005/097672 | 10/2005 |
| WO | 2007047315 | 4/2007 |
| WO | 2007/091633 | 8/2007 |
| WO | 2007139936 | 1/2008 |
| WO | 2008/118960 | 10/2008 |
| WO | 2007094870 | 12/2008 |

OTHER PUBLICATIONS

Sano et al., "Self-Organization of PEO-graft-Single-Walled Carbon Nanotubes in Solutions and Langmuir-Blodgett Films", 2001, Langmuir, vol. 17, pp. 5125-5128.*
Klumpp et al., "Functionalized carbon nanotubes as emerging nanovectors for the delivery of therapuetics", 2006, Biochimica et Biophysica Acta, pp. 404-412, available online Nov. 9, 2005.*
Liu, et al., "Supramolecular Chemistry on Water-Soluble Carbon Nanotubes for Drug Loading and Delivery", ACS Nano., 1:2007, pp. 50-56.
International Search Report and Written Opinion for PCT/US2008/078776, mailed Nov. 19, 2009.
Li et al., "A novel in situ deprotection/coupling and iterative divergent/convergent strategy for the synthesis of oligo(1,4-phenyleneethynylene)s", Tetrahedron Lett. 2005, 46, 8971-8973.
Moore et al., "Individually suspended single-walled carbon nanotubes in various surfactants", Nano Lett. 2003, 10, 1379.
Hudson et al., "Triazenes as a stable diazonium source for use in functionalizing carbon nanotubes in aqueous suspensions", J. M. Chem Mater. 2006, 18, 2766.
Chen et al., "Soluble ultra-short single-walled carbon nanotubes", J. Am. Chem. Soc. 2006, 32, 10568.
Nakamura, et al. "Oral Insulin Delivery Using P(MAA-g-EG) Hydrogels: Effects of Network Morphology on Insulin Delivery Characteristics" J. Control. Release 2004, 95, 589-599.
Park, et al., "Mechanisms of Mucoadhesion of Poly(acrylic acid) Hydrogels" Pharm. Res. 1987, 4, 457-464.
Serra, et al. "Design of Poly(ethylene glycol)-Tethered Copolymers as Novel Mucoadhesive Drug Delivery Systems" Eur. J. Pharm. Biopharm. 2006, 63, 11-18.
Wirth, et al., "Lectin-Mediated Drug Delivery: Influence of Mucin on Cytoadhesion of Plant Lectins in Vitro" J. Control. Release 2002, 79, 183-191.
Liu et al., "Fullerene Pipes," Science, 280, pp. 1253-1256 (1998).
Chen et al., "Solution Properties of Single-Walled Carbon nanotubes," Science, 282, pp. 95-98 (1998).

(Continued)

*Primary Examiner* — James Rogers
(74) *Attorney, Agent, or Firm* — Winstead PC

(57) ABSTRACT

Compositions comprising a plurality of functionalized carbon nanotubes and at least one type of payload molecule are provided herein. The compositions are soluble in water and PBS in some embodiments. In certain embodiments, the payload molecules are insoluble in water. Methods are described for making the compositions and administering the compositions. An extended release formulation for paclitaxel utilizing functionalized carbon nanotubes is also described.

18 Claims, 6 Drawing Sheets

(56) References Cited

OTHER PUBLICATIONS

Khabashesku et al., "Fluorination of Single-Wall Carbon Nanotubes and Subsequent Derivatization Reactions," Acc. Chem. Res., 35, pp. 1087-1095 (2002).
Sun et al., "Functionalized Carbon Nanotubes: Properties and Applications," Acc. Chem. Res., 35, pp. 1096-1104 (2002).
Holzinger et al., "Sidewall Functionalization of Carbon Nanotubes," Angew. Chem. Int. Ed., 40(21), pp. 4002-4005 (2001).
Bahr et al., "Covalent chemistry of single-wall carbon nanotubes," J. Mater. Chem., 12, pp. 1952-1958 (2002).
Gu et al., "Cutting Single-Wall Carbon Nanotubes through Fluorination," Nano Letters, 2(9), pp. 1009-1013 (2002).
O'Connell et al., "Reversible water-solubilization of single-walled carbon nanotubes by polymer wrapping," Chem. Phys. Lett., 342, pp. 265-271 (2001).
Dyke et al., "Solvent-Free Functionalization of Carbon Nanotubes," J. Am. Chem. Soc., 125, pp. 1156-1157 (2003).
Dyke et al., "Unbundled and Highly Functionalized Carbon Nanotubes from Aqueous Reactions," Nano Lett., 3, pp. 1215-1218 (2003).
Rinzler et al., "Large-Scale Purification of Single-Walled Carbon Nanotubes: Process, Product, and Characterization," Appl. Phys. A, 67, pp. 29-37 (1998).
Zimmerman et al., "Gas-Phase Purification of Single-Wall Carbon Nanotubes," Chem. Mater., 12(5), pp. 1361-1366 (2000).
Chiang et al., "Purification and Characterization of Single-Wall Carbon nanotubes," J. Phys. Chem. B, 105, pp. 1157-1161 (2001).
Chiang et al., "Purification and Characterization of Single-Wall Carbon Nanotubes (SWNTs) Obtained from the Gas-Phase Decomposition of CO (HiPco Process)," J. Phys. Chem. B, 105, pp. 8297-8301 (2001).
Farkas et al., "Length sorting cut single wall carbon nanotubes by high performance liquid chromatography," Chem. Phys. Lett., 363, pp. 111-116 (2002).
Chattopadhyay et al., "A Route for Bulk Separation of Semiconducting from Metallic Single-Wall Carbon nanotubes," J. Am. Chem. Soc., 125, 3370-3375 (2003).
Bachilo et al., "Structure-Assigned Optical Spectra of Single-Walled Carbon Nanotubes," Science, 298, 2361-2366 (2002).
Strano et al., "Electronic Structure Control of Single Walled Carbon Nanotube Functionalization," Science, 301, pp. 1519-1522 (2003).
Um, et al., "The synthesis and properties of triazine-stilbene fluorescent brighteners containing the phenolic antioxidant [II]", Dyes and Pigments, 2006, 70, 84.
Kari et al., "Zebrafish: An emerging model system for human disease and drug discovery," Nature, 2007, 82(1), 70-80.
Pamujula et al., "Oral delivery of spray dried PLGA/amifostine nanoparticles," Journal of Pharmacy and Pharmacology, 2004, 56, 1119-1125.
International Search Report and Written Opinion, PCT/US2008/058268, Feb. 26, 2009.

\* cited by examiner

| IN VITRO IC DATA IN Tu167 AND UMSCCI CELL LINES | | | |
|---|---|---|---|
| COMPOUND | VEHICLE | Tu167 $IC_{50}(nm):R^2$ | UMSCCI $IC_{50}(nm):R^2$ |
| PACLITAXEL | CREMAPHOR | 0.62 (0.88) | 0.26 (0.91) |
| 3 | AQUEOUS | 2.7 (0.96) | --- |
| 3 | AQUEOUS | 2.0 (0.86) | --- |
| 3 | AQUEOUS | --- | 2.6 (0.95) |
| 2 | AQUEOUS | --- | NO EFFECT |

Fig. 9

WATER-SOLUBLE CARBON NANOTUBE COMPOSITIONS FOR DRUG DELIVERY AND MEDICINAL APPLICATIONS

CROSS-REFERENCE TO RELATED APPLICATIONS

This application is a continuation-in-part of International Application No. PCT/US2008/058268, filed Mar. 26, 2008, which claims the benefit of U.S. provisional patent applications 60/908,115, filed Mar. 26, 2007, and 60/977,311, filed Oct. 3, 2007. This application further claims priority to U.S. provisional patent application 60/977,311, filed Oct. 3, 2007, which is incorporated by reference as if written herein in its entirety.

STATEMENT REGARDING FEDERALLY SPONSORED RESEARCH

This invention was made with government support under Grant No. DE-FC36-05GO15073, awarded by the U.S. Department of Energy; Grant No. NNJ06HE06A, awarded by the National Aeronautics and Space Administration; Grant No. NNJ06HI25A, awarded by the National Aeronautics and Space Administration; Grant No. NNJ05HE75A, awarded by the National Aeronautics and Space Administration; and Grant No. HR0011-08-1-0010, awarded by the U.S. Department of Defense. The Government has certain rights in the invention.

BACKGROUND

In spite of the wide structural diversity exhibited by drug molecules, many drugs and promising drug candidate molecules are highly hydrophobic. Drug hydrophobicity makes formulation of drugs in aqueous-based solvents difficult, particularly for oral gavage or intravenous dosing. Biocompatible aqueous-based solvents for drug dissolution and drug delivery may include, for example, sterile water for injection, normal saline, phosphate buffered saline (PBS), Ringers Lactate, and 5% aqueous dextrose solution. Various organic co-solvents and surfactants may be added to solubilize drug molecules in a predominantly aqueous medium. These co-solvents and surfactants may include DMSO, propylene glycol, ethanol, poly(ethylene glycol) (PEG), poly(propylene glycol) (PPG), cremaphor, and TWEEN®. Current needs in drug formulation practice include reducing drug toxicity, increasing in vivo absorption, and improving drug release profiles, particularly through extended release formulations.

Formulation of drug compounds in biocompatible aqueous media is desirable for patient administration. Certain organic co-solvents, such as cremaphor, are known to produce toxic side effects in certain patient groups. When formulating a drug, a practitioner must weigh the benefit offered by the drug in comparison to potential toxic effects produced by the dissolution vehicle.

In view of the foregoing, non-toxic means for dissolving drugs in aqueous media would provide considerable patient benefit. Non-toxic means for dissolving drugs, which also provide extended release of the drug compounds, are also of considerable benefit.

SUMMARY

In various embodiments, compositions are disclosed herein. The compositions include a plurality of functionalized carbon nanotubes and at least one type of payload molecule. The functionalized carbon nanotubes are water-soluble. The functionalized carbon nanotubes are covalently functionalized with a plurality of solubilizing groups. The at least one type of payload molecule is non-covalently associated with the functionalized carbon nanotubes.

In other various embodiments, methods are disclosed herein. The methods include providing a plurality of functionalized carbon nanotubes, dissolving the plurality of functionalized carbon nanotubes in a solvent, and adding at least one payload molecule to the solvent to make a solution. The functionalized carbon nanotubes are water-soluble. The functionalized carbon nanotubes are covalently functionalized with a plurality of solubilizing groups. The solvent includes water. The solution comprises the at least one payload molecule and the plurality of functionalized carbon nanotubes. The at least one payload molecule is non-covalently associated with the functionalized carbon nanotubes. In some embodiments presented herein, the compositions are administered to a subject.

In some embodiments, paclitaxel extended release formulations are disclosed. The extended release formulations include a solution of functionalized carbon nanotubes and a quantity of paclitaxel. The functionalized carbon nanotubes are water-soluble. The functionalized carbon nanotubes are covalently functionalized with a plurality of solubilizing groups. The solution includes water. In certain embodiments, the solubilizing groups comprise PEG moieties.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing a specific embodiment of the disclosure, wherein:

FIG. 9 shows an embodiment of summarized in vitro $IC_{50}$ data for PEG-functionalized, paclitaxel-associated SWNTs 3, PEG-functionalized SWNTs 2, and cremaphor-solubilized paclitaxel in Tu167 and UMSCC1 cell lines.

DETAILED DESCRIPTION

Figure 1:
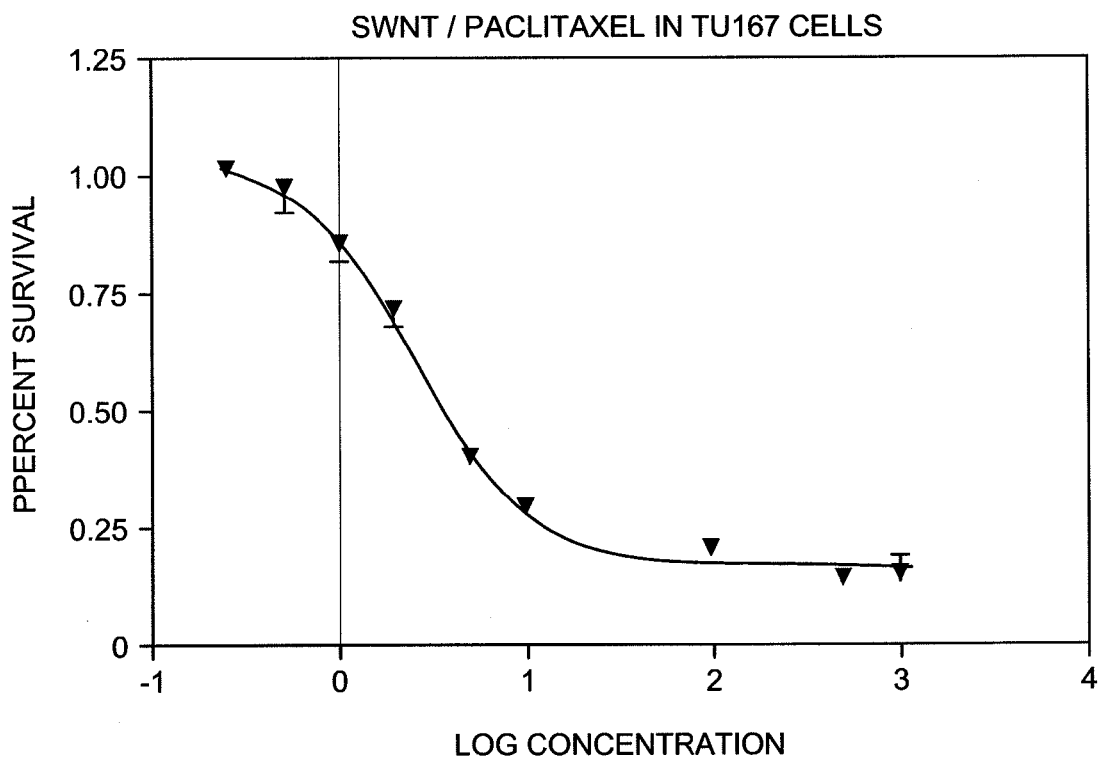
FIG. 1 shows an embodiment of the in vitro cell killing properties of PEG-functionalized, paclitaxel-associated SWNTs 3 in Tu167 cells. Paclitaxel was dissolved in acidic MeOH prior to forming 3. The MeOH was removed after forming 3.

In the following description, certain details are set forth such as specific quantities, sizes, etc. so as to provide a thorough understanding of the various embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing a particular embodiment of the disclosure and are not intended to be limiting thereto. Drawings are not necessarily to scale.

While most of the terms used herein will be recognizable to those of skill in the art, the following definitions are nevertheless put forth to aid in the understanding of the present disclosure. It should be understood, however, that when not explicitly defined, terms should be interpreted as adopting a meaning presently accepted by those of skill in the art.

"Insoluble in water or water-insoluble," as used herein, refers to a condition in which a compound is substantially undissolved in a given quantity of water. In some embodiments, a compound is water-insoluble if a stable solution having a concentration greater than about 1% (w/v) solution cannot be prepared in water. In some embodiments, a compound is water-insoluble if a stable solution having a concentration greater than about 0.1% (w/v) cannot be not be prepared in water. In still other embodiments, a compound is water-insoluble if a stable solution having a concentration greater than 0.01% (w/v) cannot be prepared in water. "Stable solution," as used hereinabove, refers to a solution whose concentration does not change more than about 10% over about five days at room temperature.

"Non-covalent association or non-covalently associated," as used herein, refers to a molecular interaction not including a covalent bond between two or more moieties. Non-covalent associations may include, but are not limited to, ionic interactions, acid-base interactions, hydrogen bonding interactions, π-stacking interactions, van der Waals interactions, adsorption, physisorption, and sequestration.

Various embodiments presented hereinbelow refer to carbon nanotubes. In the various embodiments presented hereinbelow, the carbon nanotubes may be formed by any known technique and can be in a variety of forms, such as soot, powder, fibers, and bucky paper. Carbon nanotubes may be any length, diameter, or chirality produced by any of the various production methods. Carbon nanotubes may include, but are not limited to, single-wall carbon nanotubes (SWNTs), double-wall carbon nanotubes (DWNTs), multi-wall carbon nanotubes (MWNTs), shortened carbon nanotubes, oxidized carbon nanotubes, functionalized carbon nanotubes, and combinations thereof. One skilled in the art will recognize that any embodiments for SWNTs provided hereinbelow may be practiced equivalently within the spirit and scope of the disclosure with DWNTs and MWNTs.

Functionalized carbon nanotubes, as used herein, refers to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In certain embodiments of the disclosure, carbon nanotubes are functionalized by oxidative cleavage to introduce carboxylic acid groups, followed by reaction of the carboxylic groups to covalently bond a plurality of solubilizing groups to the carbon nanotube. The solubilizing groups may be poly(ethylene glycol) (PEG) moieties in an embodiment.

In various embodiments, compositions are disclosed herein. The compositions include a plurality of functionalized carbon nanotubes and at least one type of payload molecule. The functionalized carbon nanotubes are water-soluble. The functionalized carbon nanotubes are covalently functionalized with a plurality of solubilizing groups. In certain embodiments, the plurality of solubilizing groups is covalently attached to the carbon nanotube through amide bonds. The at least one type of payload molecule is non-covalently associated with the functionalized carbon nanotubes. In some embodiments of the compositions, the non-covalent association does not include π-stacking of the at least one type of payload molecule with the functionalized carbon nanotubes.

In various embodiments, the compositions are soluble in aqueous PBS buffer. Certain shortened carbon nanotubes may possess water solubility but are insoluble in PBS buffer. The compositions are advantageous over other such carbon nanotubes in this regard because of the PBS buffer solubility rendered by the plurality of solubilizing groups. Further, the solubilizing groups contribute to the non-covalent association of the payload molecules. One skilled in the art will recognize that solubility in biocompatible aqueous delivery systems is favorable for in vivo applications. PBS buffer represents an exemplary biocompatible aqueous delivery system. The compositions provided herein may be dissolved in other biocompatible aqueous delivery systems known to those skilled in the art, and solubility of the compositions in PBS should not be considered limiting with regard to use of the compositions. The dissolved compositions may be administered to a subject, for use in applications such as treating a disease or imaging a tissue.

In certain embodiments of the compositions, the functionalized carbon nanotubes comprise single-wall carbon nanotubes. One skilled in the art will recognize that the compositions disclosed herein may substitute DWNTs and MWNTs for SWNTs. Substituting functionalized DWNTs and MWNTs for functionalized SWNTs fully resides within the spirit and scope of the disclosure.

In some embodiments of the compositions, the at least one type of payload molecule is insoluble in water. Many organic, organometallic and coordination compounds are hydrophobic and highly insoluble in water. Solubilization of water-insoluble compounds is a beneficial property of the compositions for use in a number of applications. An exemplary application comprises use of the compositions as a drug delivery system. A number of drug compounds are substantially water-insoluble and necessitate specialized vehicles for dissolution prior to administration to a subject. An exemplary vehicle often used for dissolution of water-insoluble drugs is cremaphor. Although cremaphor can solubilize a number of drug compounds, certain patients experience toxic side effects when given cremaphor-solubilized drugs. The compositions disclosed herein are advantageous for solubilizing drug compounds through non-covalent association, including those that are exceedingly water-insoluble, such as paclitaxel. Further, the compositions are advantageous in that the functionalized carbon nanotubes themselves are non-toxic to cells. This property, along with their solubility in biocompatible aqueous delivery systems, such as PBS buffer, makes the compositions viable for in vivo drug delivery.

The solubilizing groups of the functionalized carbon nanotubes facilitate dissolution of the functionalized carbon nanotubes in solvents comprising water. Solubilizing groups may include, but are not limited to, acidic or basic groups that may form water-soluble salts. In other embodiments, solubilizing groups may include groups capable of forming hydrogen bonds with the water solvent, such as certain carbohydrate moieties. In other embodiments, the solubilizing groups may be a water-soluble polymer. Exemplary water soluble polymers may include poly(ethylene oxide) (PEO), poly(propylene oxide) (PPO), poly(ethylene imine) (PEI), and derivatives and combinations thereof. In various embodiments of the compositions, the solubilizing groups include at least one moiety selected from a group consisting of PEG moieties, PPO moieties, PEI moieties, and synthetic derivatives thereof. Derivatized water-soluble polymers, such as functionalized PEG derivatives, may be prepared using techniques known to those skilled in the art. Exemplary but non-limiting examples of derivatized water-soluble polymers suitable for preparing water-soluble functionalized carbon nanotubes are described hereinbelow as experimental examples.

In certain embodiments of the compositions, the PEG moieties have an average molecular weight greater than about 400. In other embodiments of the compositions, the PEG moieties have an average molecular weight greater than about 2000. In still other embodiments of the compositions, the PEG moieties have an average molecular weight greater than about 5000. One skilled in the art will understand that PEG can be made with different degrees of polymerization to produce polymers having various average molecular weights. Likewise, other polymers can be made with various average molecular weights. One skilled in the art will further recognize that PEG having different molecular weights will possess differing properties. As such, the various molecular weight PEG moieties may confer differing properties to the functionalized carbon nanotubes following covalent attachment of the PEG moieties to the carbon nanotubes. Differing properties conferred by various molecular weight PEG moieties in the compositions disclosed herein may include such properties as, but not limited to, aqueous solubilities, payload association capacities, and payload release rates.

In some embodiments of the compositions, the functionalized carbon nanotubes include at least one tissue-targeting moiety. Use of tissue-targeting moieties is well known in the art to provide directed delivery of a drug to a particular tissue in vivo, such as a tumor tissue. The compositions may also be directed to certain cellular receptors, such as through receptor ligands attached to the functionalized carbon nanotube. In some disease states, such as but not limited to cancer, certain cellular receptors are either overexpressed or in a high-activity binding state. Direction of the compositions herein to cellular receptors advantageously provides a means of targeting a particular tissue. In some embodiments of the compositions, the at least one tissue-targeting moiety is selected from a group including, but not limited to, aptamers, antibodies, antibody fragments, saccharides, peptides, proteins, hormones, receptor ligands, and synthetic derivatives thereof. Various cellular recognition sites exist for these moieties, allowing for directed tissue targeting of the compositions.

The tissue targeting moiety may include at least one folate moiety in an embodiment. An exemplary but non-limiting folate moiety disclosed herein is shown below. Preparation of this exemplary folate moiety and attachment to a functionalized carbon nanotube is presented hereinbelow as an experimental example.

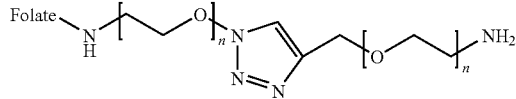

In some embodiments of the compositions, the at least one type of payload molecule is selected from a group consisting of a drug molecule, a radiotracer molecule, a radiotherapy molecule, a diagnostic imaging molecule, a fluorescent tracer molecule, a protein molecule, and combinations thereof. In various embodiments the at least one type of payload molecule is insoluble in water. The various composition embodiments are advantageous in providing water solubility to a wide variety of drug, radiotracer, radiotherapy, imaging, tracer and protein molecules that are otherwise insoluble in water. The compositions are further advantageous for these moieties because of the non-toxicity of the functionalized carbon nanotubes containing solubilizing moieties. As such, in various embodiments, the compositions may be delivered to a living subject for imaging or therapy purposes. One skilled in the art will recognize the advantages of the compositions when delivered to a living subject, as compared to typically-used drug delivery vehicles, such as cremaphor.

Exemplary types of drug molecules that may be non-covalently associated with the water-soluble carbon nanotubes disclosed herein may include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitors, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids. bronchodilator, antiallergics, mucolytics, corticosteroids, beta-receptor antagonists, anticholinergics, steroids, androgens, antiandrogens, growth hormones, thyroid hormones, antithyroid drugs, vasopressin analogues, antibiotics, antifungals, antituberculous drugs, antimalarials, antiviral drugs, antiprotozoal drugs, radioprotectants, chemotherapy drugs, cytostatic drugs, and cytotoxic drugs. In various embodiments of the compositions, the at least one type of payload molecule comprises paclitaxel.

Radiotracer and radiotherapy molecules that may be non-covalently associated with the water soluble carbon nanotubes herein may include, but are not limited to, organic compounds and coordination compounds prepared from commonly used nuclear medicine isotopes. These compounds may include those used in therapeutic nuclear medicine and diagnostic imaging, such as SPECT and PET imaging. Exemplary but non-limiting radioisotopes that may form the compounds that may be non-covalently associated in the compositions herein may include $^{99m}$Tc, $^{123}$I, $^{131}$I, $^{201}$Tl, $^{67}$Ga, $^{18}$F, $^{111}$In, $^{177}$Lu, $^{90}$Y, $^{64}$Cu, and $^{67}$Cu.

In addition to diagnostic nuclear medicine molecules, diagnostic imaging molecules may include those for MRI contrast enhancement or X-ray contrast enhancement. MRI contrast enhancement agents that may be non-covalently associated in the compositions disclosed herein include, but are not limited to, Gd chelates. X-ray contrast agents that may be non-covalently associated in the compositions disclosed herein include, but are not limited to, poly-iodinated organic compounds. Exemplary fluorescent tracers that may be non-covalently associated in the compositions disclosed herein include, but are not limited to, fluorescein and any of its analogs.

Various protein molecules may be non-covalently associated in the compositions disclosed herein. An exemplary protein molecule that may form the compositions is EGF, which binds to the EGF receptor. In various embodiments of the compositions, the at least one type of payload molecule comprises the protein EGF.

From the foregoing discussion, it will be evident to one skilled in the art that a wide variety of molecules can be non-covalently associated in the various compositions disclosed herein. The exemplary embodiments disclosed herein are merely representative of a general approach for non-covalently associating any of a wide variety of drug molecules of various functional and structural classes, radioimaging and radiotherapy agents, non-radioactive imaging agents, and proteins. The ability to sequester virtually any type of payload molecule at will within functionalized carbon nanotubes provides an avenue for improved biodistribution and toxicity profiles of a number of small molecule drugs and proteins. Further embodiments of the compositions and the advantages thereof are discussed below.

In certain embodiments of the compositions, the compositions inhibit metabolic decomposition of the at least one type of payload molecule. Since the payload molecules are effectively sequestered from their surrounding environment by non-covalent association with the solubilizing groups of the functionalized carbon nanotubes, metabolizing enzymes (such as cytochromes) are limited from attacking the payload molecules. Thus, for a given quantity of a metabolizable drug compound, the compositions disclosed herein deliver a higher quantity of parent drug compared to a comparable metabolizable formulation. This advantageous property allows lower drug doses to be administered to a patient, potentially providing reduced toxic side effects from the drug itself.

In certain other embodiments of the compositions, the compositions provide extended in vivo release of the at least one type of payload molecule. Extended in vivo release comprises a greater in vivo residence time of the at least one type of payload molecule compared to that of the at least one type of payload molecule alone. Since the payload molecules are non-covalently associated with the solubilizing groups of the functionalized carbon nanotubes, the payload molecules will only slowly diffuse out of the composition and become available in vivo. The properties of the compositions may be altered as described hereinabove to provide either a faster or slower rate of diffusion release for a given application. Applicant has demonstrated that the payload molecules are non-covalently associated with the compositions, and the payload molecules are subject to slow diffusion from the compositions. For example, when the fluorescent molecule fluorescein isothiocyanate (FITC) was associated with the compositions, prolonged dialysis in water (1-2 months) only slowly diminished the composition fluorescence. However, when the dialysis was performed in hot DMF for 1 week, all the fluorescence of the compositions was quickly removed. This demonstration shows that that the carbon nanotube/solubilizing group matrix solubilizes the FITC by sequestering it from surrounding water within the more solubilizing organic environment of the matrix. As demonstrated hereinbelow in a non-limiting example, the at least one type of payload molecule for the compositions can be paclitaxel. The paclitaxel is released from the compositions in vivo to produce comparable tumor growth inhibition to cremaphor-solubilized paclitaxel.

In certain embodiments, the compositions provide intracellular delivery of the at least one type of payload molecule. The intracellular delivery may occur in vitro or in vivo. Applicant has demonstrated that FITC can be non-covalently associated with the compositions disclosed hereinabove. When provided to cells, the cells became fluorescent, demonstrating that the FITC entered the cells. In contrast, when either FITC alone or FITC/PEG was provided to cells, no intracellular fluorescence was observed. Thus, the compositions provide intracellular delivery of the at least one type of payload molecule.

In other various embodiments, methods are disclosed herein. The methods include providing a plurality of functionalized carbon nanotubes, dissolving the plurality of functionalized carbon nanotubes in a solvent, and adding at least one payload molecule to the solvent to make a solution. The functionalized carbon nanotubes are water-soluble. The functionalized carbon nanotubes are functionalized with a plurality of solubilizing groups. The solvent includes water. The solution comprises the at least one payload molecule and the plurality of functionalized carbon nanotubes. The at least one payload molecule is non-covalently associated with the functionalized carbon nanotubes. Payload molecule association with the carbon nanotube solubilizing groups, for example PEG, can also aid in the non-covalent association capability of the functionalized carbon nanotube system. In certain embodiments of the methods, the methods further comprise administering the solution to a subject, for example, for treating or monitoring a disease or condition. In various embodiments of the methods, the functionalized carbon nanotubes are soluble in aqueous PBS buffer. As discussed hereinabove, solubility in biocompatible aqueous delivery systems is advantageous for administering drugs to living subjects. In various embodiments of the methods, the administering step occurs by a route selected from orally, parenterally, intravenously, intraperitoneally, intramuscularly, and subcutaneously. In some embodiments of the methods, the at least one payload molecule is delivered intracellularly following the administering step.

In various embodiments of the methods, the at least one payload molecule is dissolved in at least one solvent prior to the adding step. Various solvents may be chosen for dissolving the payload molecules, the optimal solvent choice being dictated by the solubility properties of the particular payload molecules. For adding the at least one compound to the aqueous solution of the carbon nanotubes, certain solvents demonstrating both ready solubilization properties and water miscibility may be advantageous for dissolving the payload molecules in some embodiments. Solvents with ready solubilizing capabilities and water miscibility include, but are not limited to methanol, ethanol, dimethyl sulfoxide (DMSO), and propylene glycol. In various embodiments, the methods further comprise removing the at least one solvent after the adding step. Solvents readily vaporized may be advantageous with regard to these embodiments. One skilled in the art will recognize that the list of solvents presented hereinabove is non-limiting, and any of a wide variety of solvents may be used to dissolve the payload molecules in practicing the methods herein.

In various embodiments of the methods, the at least one payload molecule is insoluble in water. The methods are advantageous in that water-insoluble compounds may be non-covalently associated with the water-soluble carbon nanotubes disclosed herein, making the compounds water soluble. As such, they are readily administered to a living subject via a non-toxic carbon nanotube vehicle in an aqueous dissolution medium.

In various embodiments of the methods, the at least one payload molecule is selected from a group consisting of a drug molecule, a radiotracer molecule, a radiotherapy molecule, a diagnostic imaging molecule, a fluorescent tracer molecule, a protein molecule, and combinations thereof. Various non-limiting examples of these different types of molecules have been previously described hereinabove. In some embodiments, the at least one payload molecule comprises paclitaxel. In some embodiments, the at least one payload molecule comprises EGF.

In various embodiments of the methods, the functionalized carbon nanotubes comprise functionalized single-wall carbon nanotubes. One skilled in the art will recognize that the methods disclosed herein may be practiced equivalently with DWNTs and MWNTs substituting for SWNTs. Such substitution fully resides within the spirit and scope of the disclosure.

In various embodiments of the methods, the solubilizing groups comprise at least one moiety selected from a group consisting of PEG moieties, PPO moieties, PEI moieties, and synthetic derivatives thereof. Use of other water-soluble polymers in practicing the method resides fully within the spirit and scope of the present disclosure.

In various embodiments of the methods, the functionalized carbon nanotubes include at least one tissue-targeting moiety. Various tissue targeting moieties that may be attached to functionalized carbon nanotubes have been discussed hereinabove. In some embodiments of the methods, the functionalized carbon nanotubes include at least one folate moiety.

In some embodiments of the methods, the methods provide an extended in vivo release of the at least one payload molecule. The extended in vivo release comprises a greater in vivo residence time for the at least one payload molecule compared to that of the at least one payload molecule alone.

In some embodiments, paclitaxel extended release formulations are disclosed. The extended release formulations include a solution of functionalized carbon nanotubes and a quantity of paclitaxel. The functionalized carbon nanotubes are water-soluble. The functionalized carbon nanotubes are functionalized with a plurality of functionalizing groups. The solution comprises water. In various embodiments, the paclitaxel is non-covalently associated with the functionalized carbon nanotubes. In various embodiments of the extended release formulations, the solution is a PBS buffer.

In various embodiments of the extended release formulations, the functionalized carbon nanotubes are functionalized single-wall carbon nanotubes. One skilled in the art will recognize that the extended release formulations may be practiced equivalently with DWNTs and MWNTs substituting for SWNTs. Such substitution fully resides within the spirit and scope of the disclosure In various embodiments, the extended release formulations may have solubilizing groups comprising at least one moiety selected from a group consisting of PEG moieties, PPO moieties, PEI moieties, and synthetic derivatives thereof. In some embodiments, the solubilizing groups comprise PEG moieties. In some embodiments of the extended release formulations, the PEG moieties have an average molecular weight greater than about 400. In other various embodiments of the extended release formulations, the PEG moieties have an average molecular weight greater than about 2000. In still other various embodiments of the extended release formulations, the PEG moieties have an average molecular weight greater than about 5000. The ability to freely vary the molecular weight of the PEG moieties advantageously allows aqueous solubility adjustment of the functionalized carbon nanotubes. Molecular weight adjustment also provides control of the strength of paclitaxel non-covalent association with the functionalized carbon nanotubes. As such, molecular weight adjustment allows one to control the release rate of paclitaxel from the extended release formulations in an embodiment. In various embodiments, the in vivo paclitaxel residence time is greater than that of paclitaxel alone.

In various embodiments, the paclitaxel extended release formulation delivers the paclitaxel intracellularly.

In various embodiments of the paclitaxel extended release formulation, the quantity of paclitaxel is at least about 1 mg of paclitaxel per 1 mL of the solution. Paclitaxel is especially water-insoluble but can be easily solubilized in extended release formulations with the water-soluble carbon nanotubes disclosed herein. For example, when 1 mg of paclitaxel dissolved in 70 μL of ethanol is added to 1 mL of water, paclitaxel immediately precipitates from solution. In contrast, when the 70 μL ethanolic solution is added to 1 mL of a solution containing PEG-functionalized carbon nanotubes, no paclitaxel precipitates from solution. The ethanol can further be removed from the water solution by evaporation, yet the paclitaxel remains in solution. Not being bound by theory or mechanism, the current understanding of the paclitaxel solubilization is that the drug is sequestered from the water and drawn into the more favorable solubilizing environment of the carbon nanotube/PEG matrix. In this way, the PEG-functionalized carbon nanotubes function analogously to a sponge withdrawing paclitaxel from the aqueous environment.

EXPERIMENTAL EXAMPLES

The following experimental examples are included to demonstrate particular aspects of the present disclosure. It should be appreciated by those of skill in the art that the methods described in the examples that follow merely represent exemplary embodiments of the disclosure. Those of skill in the art should, in light of the present disclosure, appreciate that many changes can be made in the specific embodiments described and still obtain a like or similar result without departing from the spirit and scope of the present disclosure.

Example 1

Synthesis of PEG-Functionalized SWNTs Associated with Paclitaxel

An exemplary procedure by which SWNTs can be shortened, functionalized with PEG moieties and thereafter non-covalently associated with paclitaxel is illustrated in Scheme 1.

Scheme 1: Non-covalent association of paclitaxel with a PEG-functionalized SWNT
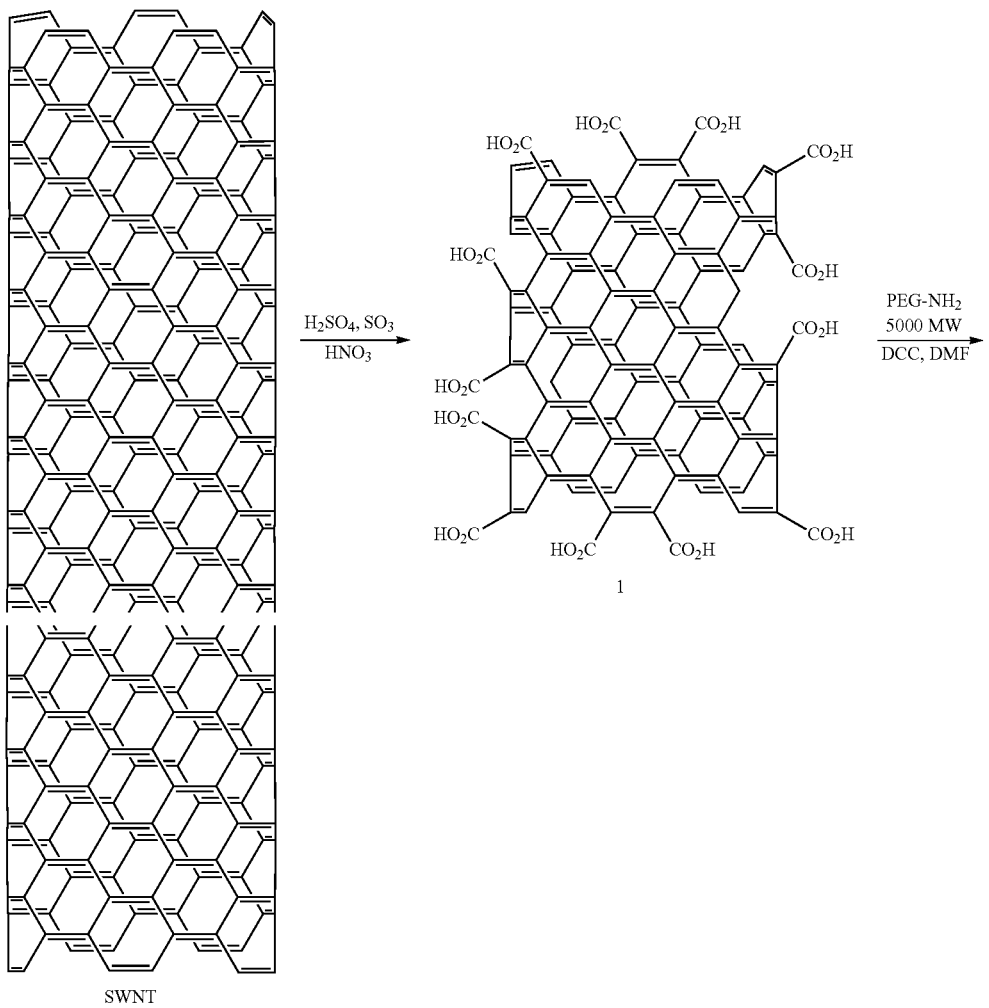
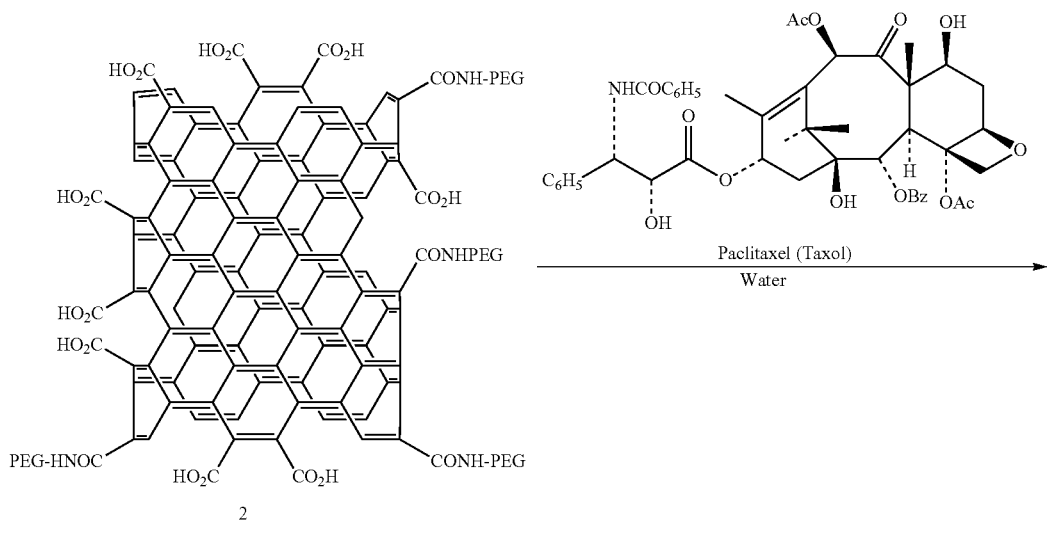

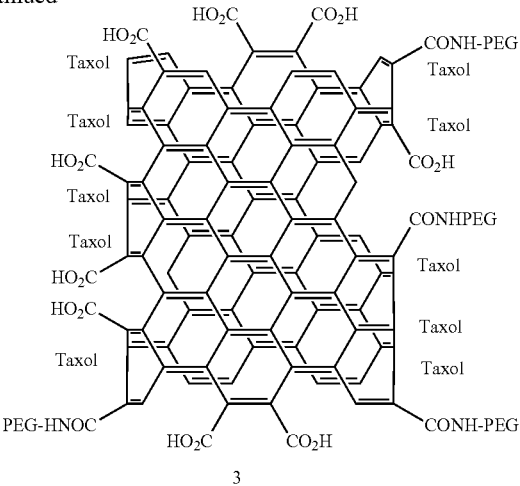

3

Cut SWNTs (1): Purified SWNTs (100 mg, 8.3 mmol) and oleum (50 mL) were added to a 300 mL Erlenmeyer flask equipped with a stir bar and stirred overnight under a nitrogen atmosphere. Nitric acid (34 mL, 70%) was poured into a 100 mL graduated cylinder. Oleum (50 mL) was then carefully added to the nitric acid and then the mixture was immediately poured into the suspension of SWNTs. Extreme caution should be taken when handling oleum. The mixture was stirred for 2 hours at 70° C. and then quenched over 500 g of ice. The mixture was then filtered over a polycarbonate membrane (0.22 μm). The moist material was neutralized by resuspension in a minimal amount of methanol, and then ethyl ether (300 mL) was added to flock the cut SWNTs. The neutralization step was repeated until the ethyl ether pH was neutral once the cut SWNTs 1 were finished filtering.

PEG functionalization of cut SWNTs (2): An oven dried 100 mL round bottom flask equipped with a stir bar was charged with 1 (0.063 g, 5.2 mmol) and anhydrous N,N-dimethylformamide (DMF) (50 mL). The mixture was vigorously stirred for 15 min under a nitrogen atmosphere. N,N'-dicyclohexylcarbodiimide (DCC, 1.08 g, 5.2 mmol) was added, followed by amine-terminated poly(ethylene glycol) (0.50 g, 0.1 mmol MW 5000), and a few pellets of DMAP (4-(dimethylaminopyridine)). The mixture was stirred overnight and purified by dialysis in water (MWCO membrane 50,000) for 5 days. The solution of 2 was filtered through layered kimwipes and used without further purification.

Associated paclitaxel PEG-functionalized SWNTs (3): PEG-functionalized SWNTs 2 (0.05 mg/mL) were added to a 5 mL glass vial equipped with a stir bar. Paclitaxel (1 mg) was dissolved in ethanol (70 μL) and added into the stirring mixture. The solution was stirred for 10 minutes and then sonicated in a bath sonicator for an additional 10 minutes to ensure full sequestration of paclitaxel. The ethanol was removed under reduced pressure, and the volume of solvent removed was replaced with an equal volume of DI water to produce PEG-functionalized, paclitaxel-associated SWNTs 3.

Example 2

Synthesis of PEG-Functionalized SWNTs Associated with EGF

An exemplary procedure by which PEG-functionalized SWNTs 2 can be non-covalently associated with EGF is illustrated in Scheme 2.

Scheme 2: Non-covalent association of EGF with a PEG-functionalized SWNT

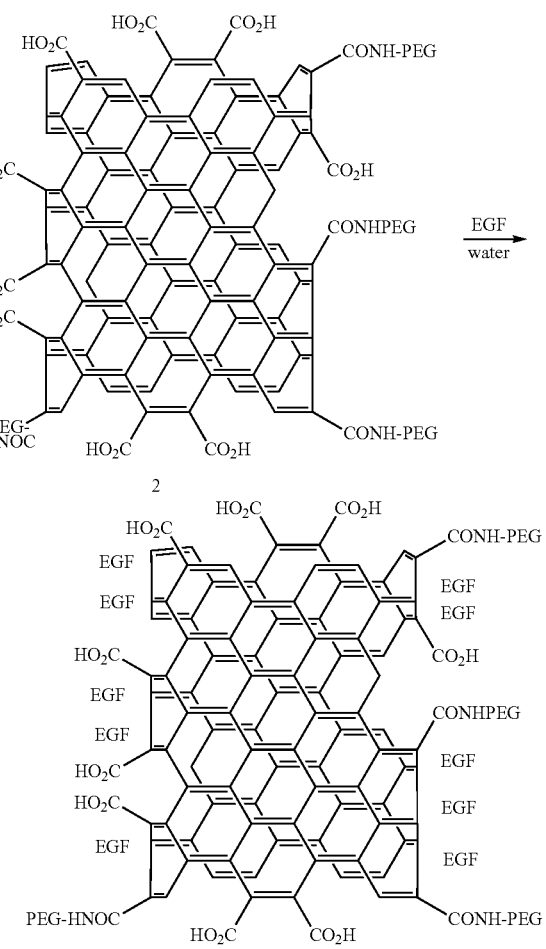

PEG-functionalized SWNTs 2 (381 mg/L, $\lambda_{max}$=763 nm, $\epsilon$=0.043) were diluted 10× with PBS. EGF (100 μg) was dissolved in 1 mL nanopure water and then diluted 10×. The diluted PEG-functionalized SWNTs 2 (6 μL) and diluted EGF (10 μL) were added together and allowed to combine for 2 hours at RT. As produced, this mixture yields 100 EGF proteins per SWNT, assuming a SWNT length of 100 nm after oxidation and 120 carbons atoms per nanometer. In another experiment, the mixture was stored at 4° C. for 3 days to allow more time for the EGF protein to associate with the PEG-functionalized SWNTs 2. The mixture was then dialyzed (MWCO membrane 50,000) in PBS to provide EGF-associated, PEG-functionalized SWNT 4.

Example 3

Synthesis of PEG-Functionalized SWNTs having a Folate Tissue-Targeting Moiety

Synthesis of amino/azido-terminated poly(ethylene glycol 5: Synthesis of compound 5 was accomplished by the method illustrated in Scheme 3.

Scheme 3: Synthesis of amino/azido-terminated poly(ethylene glycol) 5

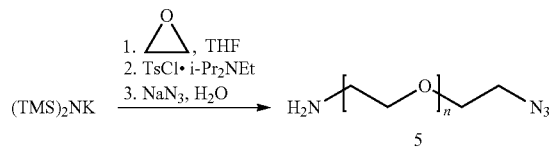

(TMS)$_2$NK (2.22 mL, 1.11 mmol) was added to an oven dried tube capped with a septum. THF (10 mL) was added and the tube was cooled to −78° C. Ethylene oxide (5 mL, 100 mmol) was condensed in a graduated cylinder containing CaH$_2$. The ethylene oxide was transferred to the pre-cooled tube using a cannula, as the graduated cylinder was heated. Once the transfer of the ethylene oxide was complete, the tube was sealed, heated to 50° C. and stirred for 14 hours. The resulting brown solution was treated with i-Pr$_2$NEt (7 mmol), and solid TsCl (635 mg, 3.33 mmol) was added in a single portion. The tube was resealed and the reaction was stirred at 50° C. for 14 hours. The reaction mixture was then poured into a solution of NaN$_3$ (975 mg, 15 mmol) in H$_2$O (100 mL) to give a biphasic mixture. The mixture was stirred at 90° C. for 4 hours, cooled to RT, washed with Et$_2$O, and extracted with CHCl$_3$. The CHCl$_3$ extracts were combined, dried over MgSO$_4$, filtered and concentrated to about 30 mL. Et$_2$O was added and the product crystallized as white needles upon standing for 14 hours in a freezer. The mother liquor was removed by filtration, and the remaining solid was washed with Et$_2$O and then dried in vacuo to give 5. (Mn=4623; Mw=5864; PDI=1.27).

Amino/propargyl-terminated poly(ethylene glycol) 6: Synthesis of compound 6 was accomplished by the method illustrated in Scheme 4.

Scheme 4: Synthesis of amino/propargyl-terminated poly(ethylene glycol) 6

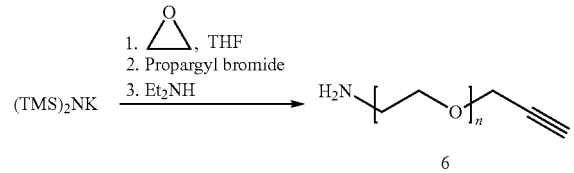

(TMS)$_2$NK (2.22 mL, 1.11 mmol) was added to an oven dried tube capped with a septum. THF (10 mL) was added and the tube was cooled to −78° C. Ethylene oxide (5 mL, 100 mmol) was condensed in a graduated cylinder containing CaH$_2$. The ethylene oxide was transferred to the pre-cooled tube using a cannula, as the graduated cylinder was heated. Once the transfer of the ethylene oxide was complete, the tube was sealed, heated to 50° C. and stirred for 14 hours. The resulting brown solution was treated with propargyl bromide (707 mg, 2.5 mmol) as an 80% solution in toluene. The tube was resealed and the reaction mixture was stirred at 50° C. for 14 hours. Et$_2$NH (0.707 mL, 6.0 mmol) was then added. The reaction was stirred for 2 hours and poured into water. The solution was washed with Et$_2$O, and extracted with CHCl$_3$. The CHCl$_3$ extracts were combined, dried over MgSO$_4$, filtered and concentrated to about 30 mL. Et$_2$O was added and the product crystallized as white needles upon standing for 14 hours in a freezer. The mother liquor was removed by filtration, and the remaining solid was washed with Et$_2$O and then dried in vacuo to give 6. (Mn=4499, Mw=5923; PDI=1.32).

Folate conjugation to amino/azido-terminated poly(ethylene glycol) 7: Folate conjugation to compound 5 was accomplished as illustrated in Scheme 5 to produce folate-functionalized, azido-terminated poly(ethylene glycol) 7.

Scheme 5: Synthesis of folate/azido-terminated poly(ethylene glycol) 7

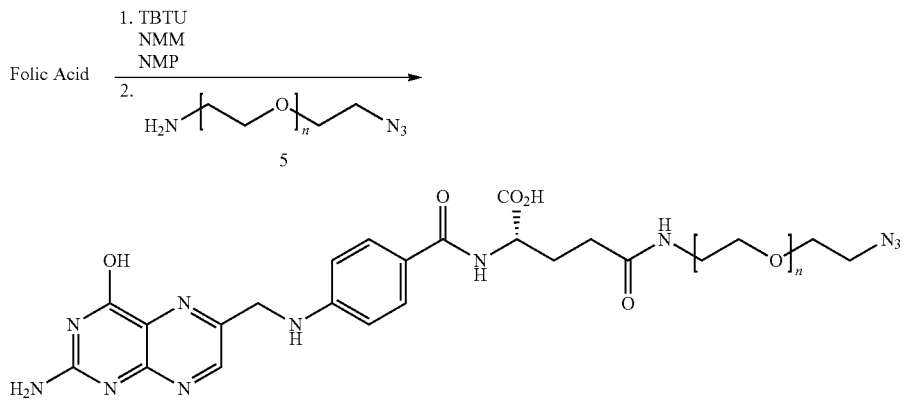

A stock solution of activated folic acid was prepared as follows: Folic acid (5 g, 10 mmol) was slowly added to a rapidly stirring solution of 4-methylmorpholine (NMM, 2.2 mL, 20 mmol), and N-methylpyrrolidone (NMP, 250 mL). The mixture was heated until all of the folic acid was dissolved and then cooled to 0° C. O-(Benzotriazol-1-yl)-N,N,N',N'-tetramethyluronium tetrafluoroborate (TBTU, 3.2 g, 10 mmol) was added and the solution was warmed to RT as it stirred for 2 hours. A portion of this solution (12.5 mL, 0.5 mmol of activated folic acid) was added to 5 (2 g, 0.34 mmol) dissolved in NMP (20 mL). The reaction was then stirred for 24 hours. $Et_2O$ was then added, producing a yellow precipitate. The reaction mixture was filtered, and the residue was washed with $Et_2O$ and EtOH. The filtrate was dialyzed in continuously flowing DI $H_2O$ for 4 days (1000 MWCO membrane). The filtrate solution was then concentrated to give 7 as a light yellow solid (1.136 g, 50%). (Mn=6024, Mw=6504, PDI=1.08).

Folate/amino-terminated poly(ethylene glycol) with a triazole linkage 8: Synthesis of folate/amino-terminated poly(ethylene glycol) having a triazole linkage 8 was accomplished as shown in Scheme 6.

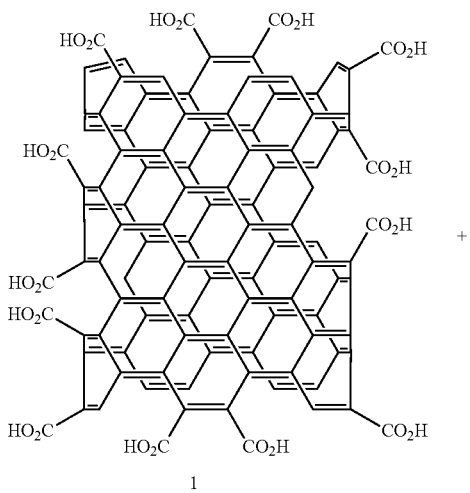

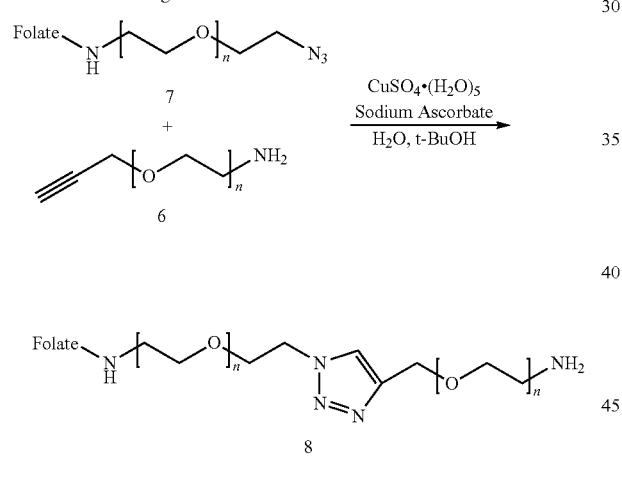

Compound 7 (494 mg, 0.08 mmol) and compound 6 (451 mg, 0.08 mmol) were combined and dissolved in $H_2O$ (7 mL) and t-BuOH (7 mL). Sodium ascorbate (30 mg, 0.15 mmol) dissolved in $H_2O$ (1.5 mL) was added to the solution, and then $CuSO_4$ pentahydrate (38 mg, 0.15 mmol) dissolved in $H_2O$ (1.5 mL) was added to the solution. The reaction turned a dark yellow/orange color. After stirring for 18 hours, the reaction was a yellow/green color. The reaction solution was dialyzed in continuously flowing DI $H_2O$ (1000 MWCO membrane), and then concentrated to give a light yellow solid 8 (839 mg, 89%).

Folate-targeted, PEG-functionalized SWNTs 9: Synthesis of folate-targeted, PEG-functionalized SWNTs was accomplished as shown in Scheme 7.

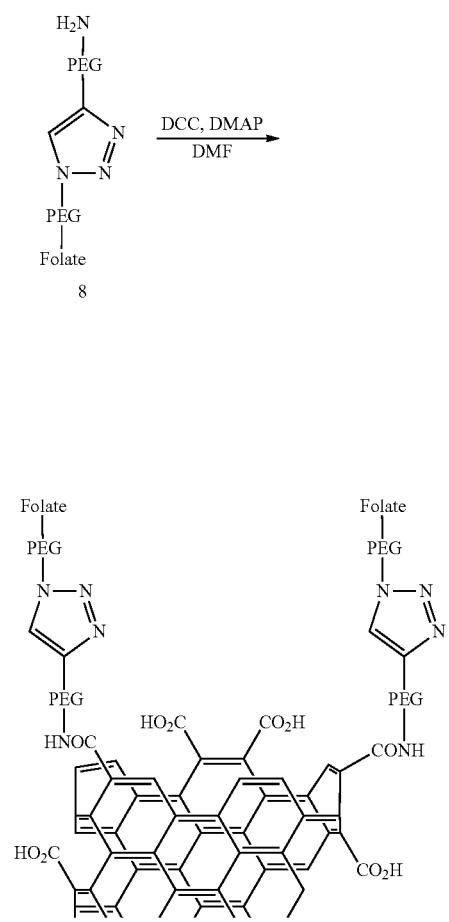

-continued

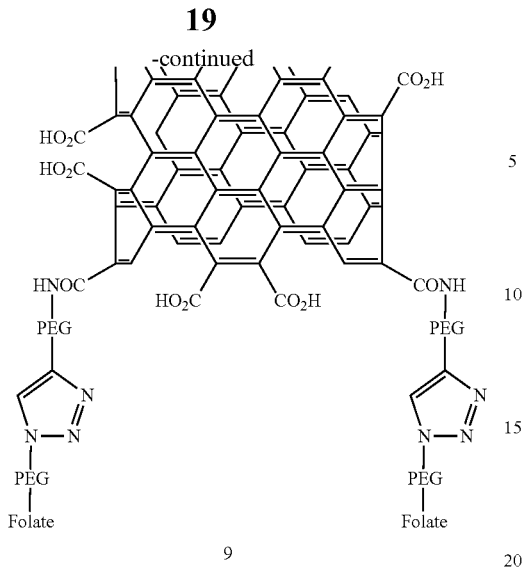

9

An oven dried flask equipped with a stir bar was charged with 1 (0.021 g, 1.7 mmol of carbon) and anhydrous N,N-dimethylformamide (DMF) (21 mL). The mixture was sonicated for 30 minutes. N,N'-dicyclohexylcarbodiimide (DCC, 0.172 g, 0.83 mmol) was added followed by 8 (0.400 g, 0.02 mmol), and a few pellets of DMAP (4-(dimethylaminopyridine)). The reaction mixture was stirred for 18 hours and then purified by dialysis for 24 hours in standing DMF (50,000 MWCO membrane), followed by dialysis in a continuous flow of DI water for 5 days. TGA analysis indicated about 1 in 102 carbons had a PEG chain.

Example 4

In Vitro Activity of PEG-Functionalized, Paclitaxel-Associated SWNTs 3

Figure 2:
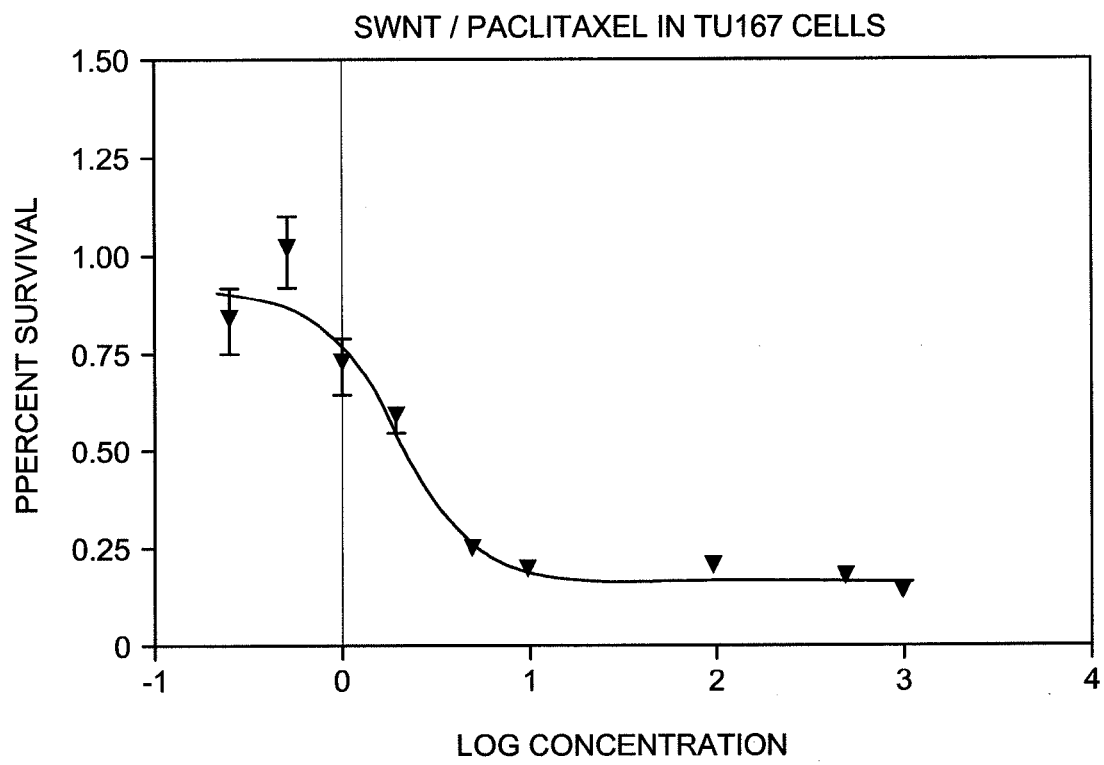
FIG. 2 shows an embodiment of the in vitro cell killing properties of PEG-functionalized, paclitaxel-associated SWNTs 3 in Tu167 cells. Paclitaxel was dissolved in neutral MeOH prior to forming 3. The MeOH was removed after forming 3.
Figure 3:
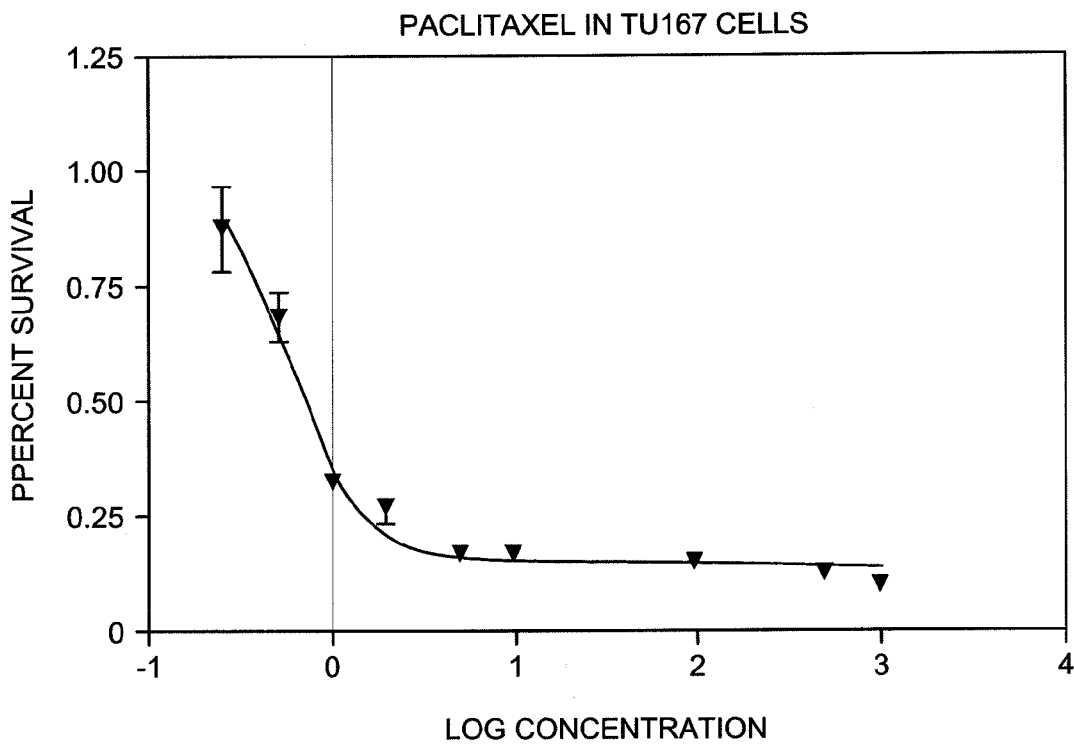
FIG. 3 shows an embodiment of the in vitro cell killing properties of cremaphor-solubilized paclitaxel in Tu167 cells.

In vitro efficacy of 3 was demonstrated by standard MTT assays in Tu167 and UMSCC1 cell lines. As shown in FIGS. 1-3, PEG-functionalized, paclitaxel-associated SWNTs 3 provided cell killing comparable to that of control paclitaxel in Tu167 cells. For the analyses, the analyses presented in FIGS. 1 and 2, the paclitaxel was dissolved in either acidic MeOH (FIG. 1) or neutral MeOH (FIG. 2) prior to association with the PEG-functionalized SWNTs. The MeOH was removed from the compositions by evaporation following sequestration of the paclitaxel by the PEG-functionalized SWNT matrix. MeOH removal was performed prior to MTT analysis. The $IC_{50}$ for 3 was comparable regardless of the method by which the paclitaxel was solubilized prior to addition to the PEG-functionalized SWNTs, as shown in FIGS. 1 and 2. The average $IC_{50}$s calculated for 3 in Tu167 cells were 2.7 nM (solubilized in acidic MeOH, FIG. 1) and 2.0 nM (solubilized in neutral MeOH, FIG. 2). Control paclitaxel displayed an $IC_{50}$ of 0.62 nM as shown in FIG. 3. The control paclitaxel was dissolved in a cremaphor vehicle.

Figure 4:
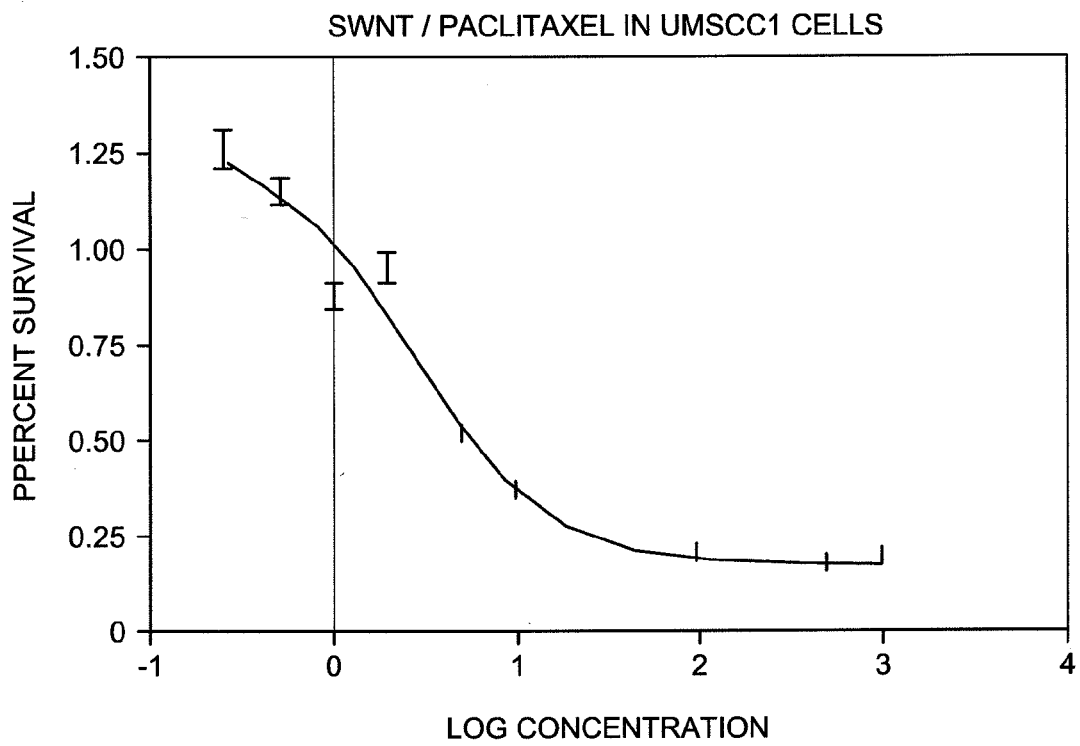
FIG. 4 shows an embodiment of the in vitro cell killing properties of PEG-functionalized, paclitaxel-associated SWNTs 3 in UMSCC1 cells.
Figure 5:
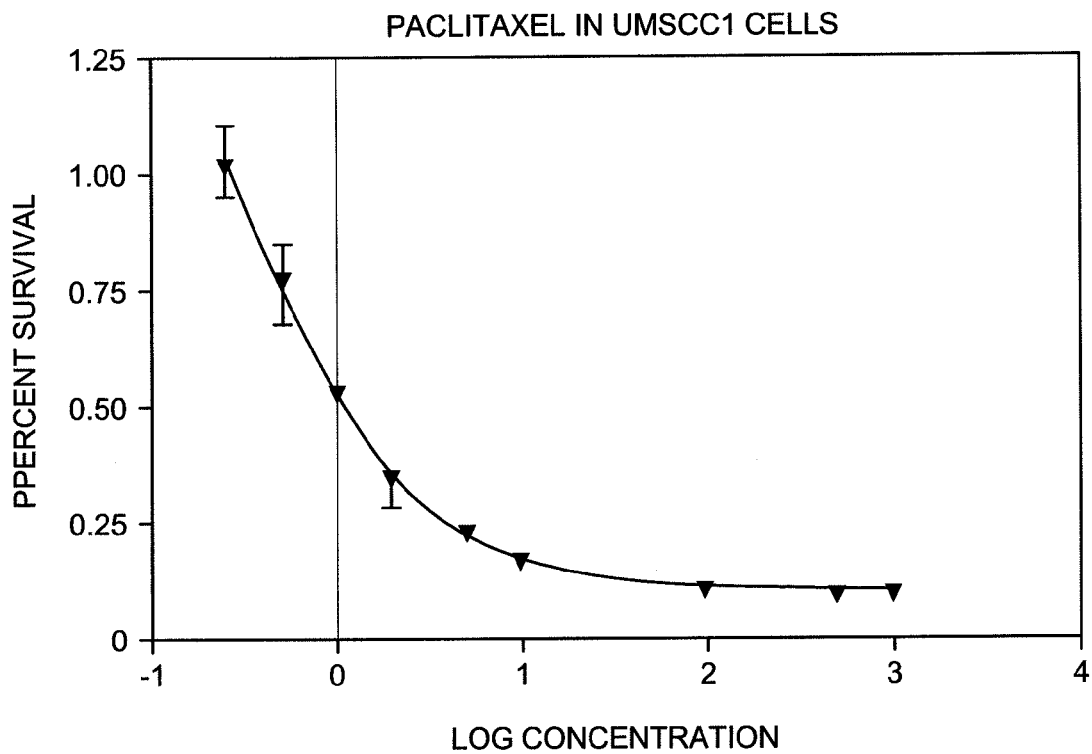
FIG. 5 shows an embodiment of the in vitro cell killing properties of cremaphor-solubilized paclitaxel in UMSCC1 cells.
Figure 6:
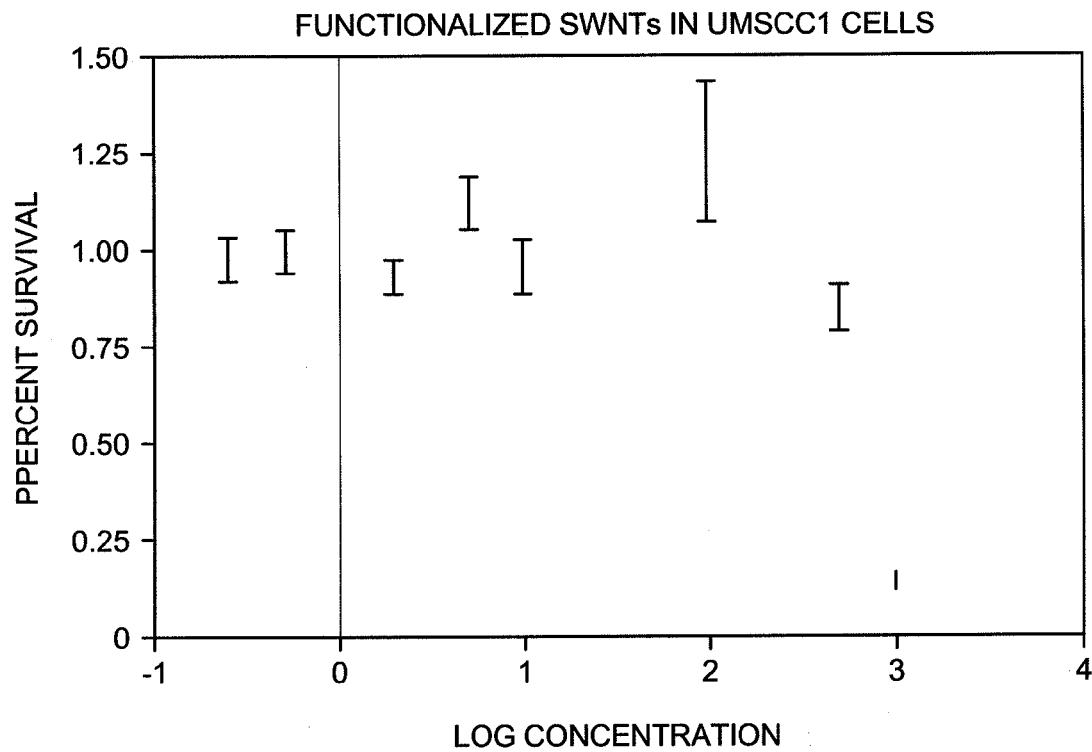
FIG. 6 shows an embodiment of the in vitro cell killing properties of PEG-functionalized SWNTs 2 in UMSCC1 cells.

As shown in FIGS. 4 and 5, PEG-functionalized, paclitaxel-associated SWNTs 3 provided cell killing comparable to that of control paclitaxel in UMSCC1 cells. For the analysis presented in FIG. 4, the paclitaxel was dissolved in EtOH prior to association with the PEG-functionalized SWNTs. The EtOH was removed from the compositions by evaporation following sequestration of the paclitaxel by the PEG-functionalized SWNT matrix. EtOH removal was performed prior to MTT analysis. The average $IC_{50}$ calculated for 3 in UMSCC1 cells was 2.6 nM. Control paclitaxel in cremaphor vehicle displayed an $IC_{50}$ of 0.26 nM as shown in FIG. 5. In contrast to the potent cell killing properties of 3, PEG-functionalized SWNTs 2 produced no effect in UMSCC1 cells as shown in FIG. 6.

FIG. 9 summarizes the $IC_{50}$ properties of 2 and 3 in Tu167 and UMSCC1 cell lines. These results demonstrate that 3 maintains cell killing properties comparable to that of control paclitaxel.

Example 5

In Vivo Activity of PEG-Functionalized, Paclitaxel-Associated SWNTs 3

Figure 7:
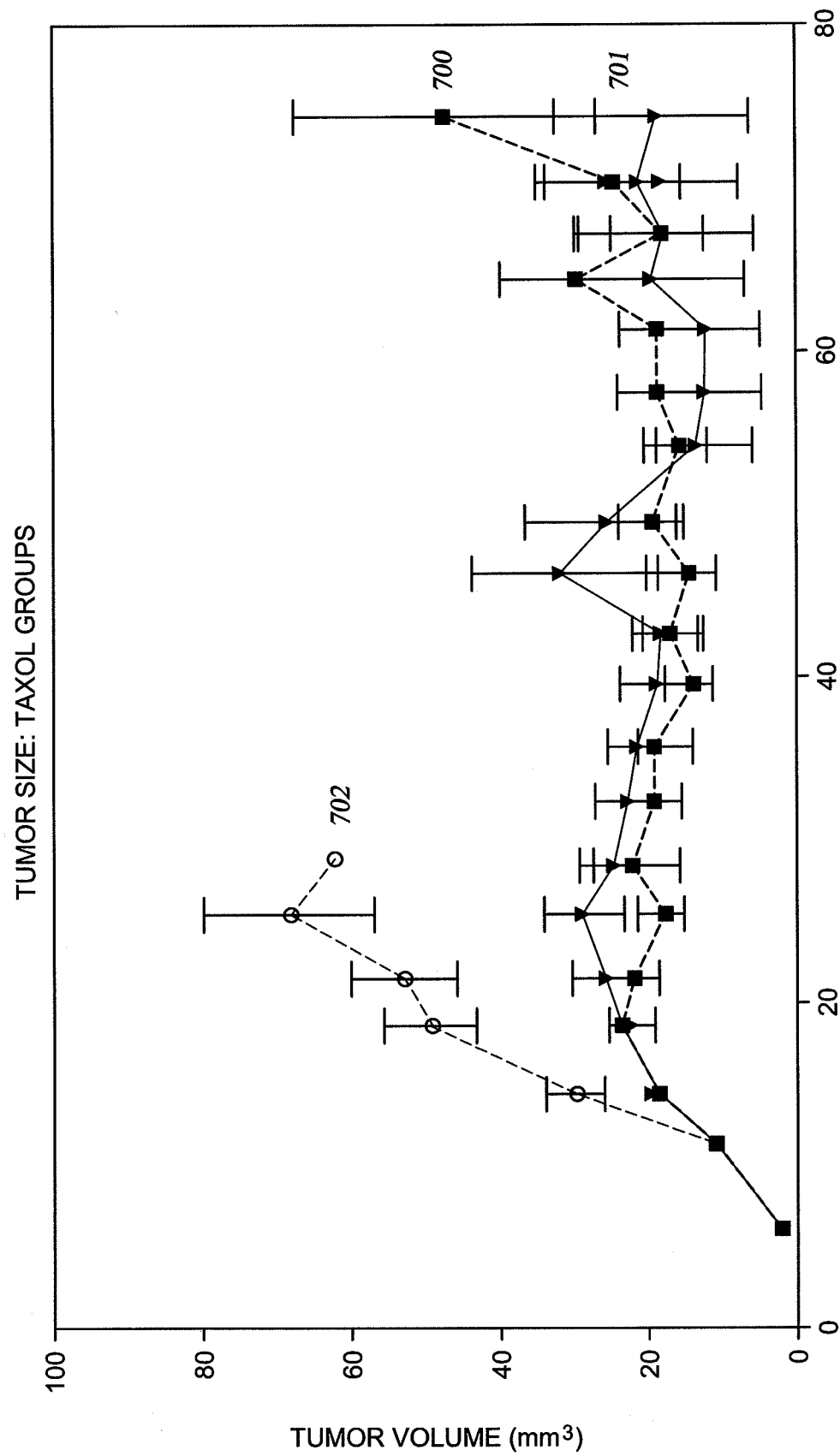
FIG. 7 shows an embodiment of the in vivo tumor growth inhibition of PEG-functionalized, paclitaxel-associated SWNTs 3 compared to a paclitaxel standard in cremaphor and drug-free control, as determined by measurement of tumor volume.
Figure 8:
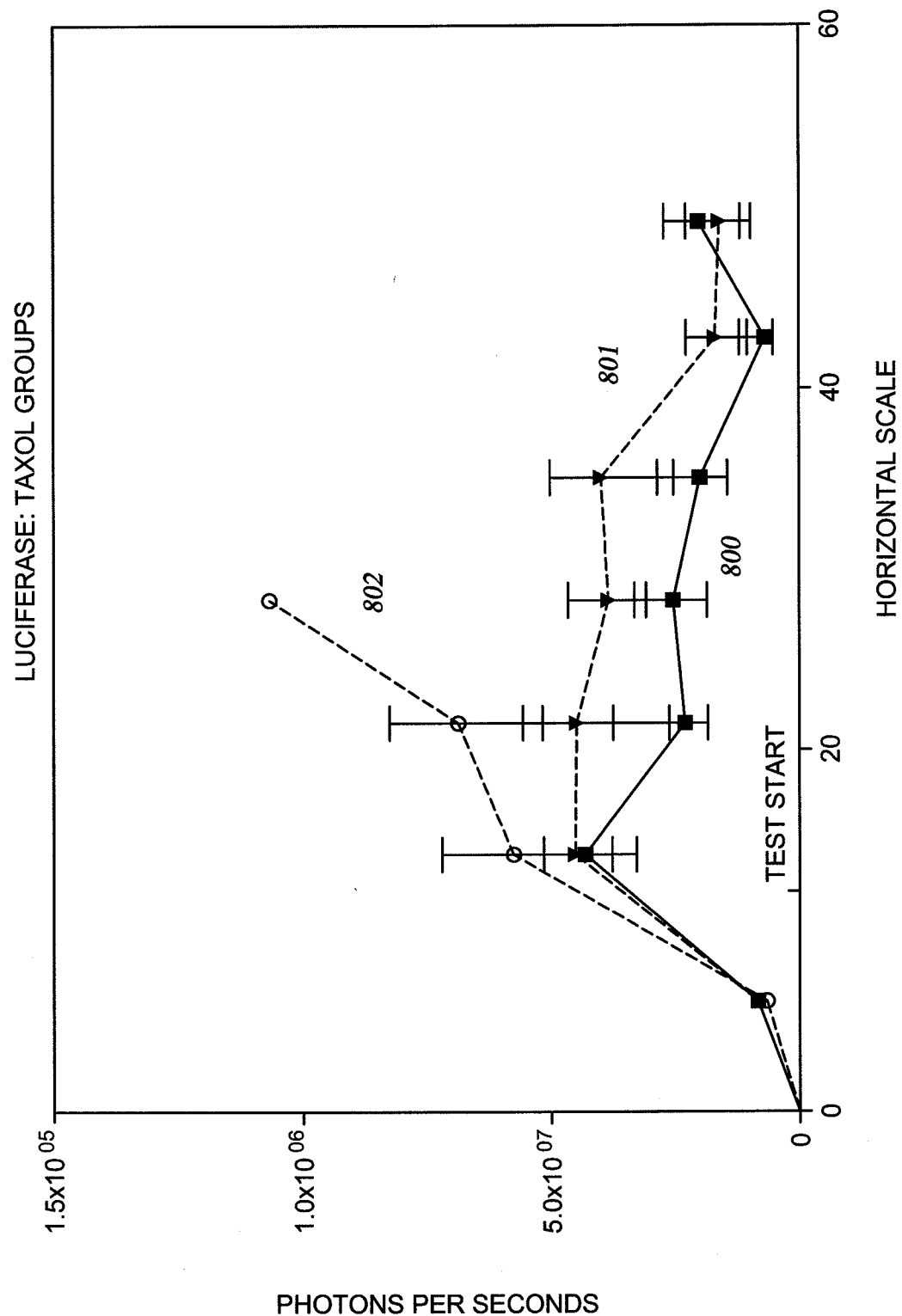
FIG. 8 shows an embodiment of the in vivo tumor growth inhibition of PEG-functionalized, paclitaxel-associated SWNTs 3 compared to a paclitaxel standard in cremaphor and drug-free control, as determined by a bioluminescence luciferase assay.

PEG-functionalized, paclitaxel-associated SWNTs displayed in vivo tumor growth inhibition as shown in FIGS. 7 and 8. FIG. 7 shows progression of tumor xenograph volume growth in the presence of paclitaxel (700) in cremophor, 3 (701), and vehicle only (702). FIG. 8 shows progression of tumor xenograph growth, as measured by a bioluminescence luciferase assay, for paclitaxel (800) in cremophor, 3 (801), and vehicle only (802). As shown by FIGS. 7 and 8, 3 maintained comparable ability to inhibit tumor growth compared to paclitaxel only.

From the foregoing description, one skilled in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A composition comprising:
   a plurality of functionalized single-wall carbon nanotubes;
      wherein the functionalized single-wall carbon nanotubes are water-soluble; and
      wherein the functionalized single-wall carbon nanotubes are covalently functionalized with a plurality of PEG moieties; and
   a drug molecule comprising paclitaxel;
      wherein the paclitaxel is insoluble in water;
      wherein the paclitaxel is non-covalently associated with the functionalized single-wall carbon nanotubes; and
   wherein the paclitaxel is sequestered from its surrounding environment by the non-covalent association with the functionalized single-wall carbon nanotubes.

2. The composition of claim 1, wherein the composition is soluble in aqueous PBS buffer.

3. The composition of claim 1, wherein the non-covalent association does not comprise π-stacking of the paclitaxel with the functionalized single-wall carbon nanotubes.

4. The composition of claim 1, wherein the PEG moieties have an average molecular weight greater than about 400.

5. The composition of claim 4, wherein the PEG moieties have an average molecular weight greater than about 2000.

6. The composition of claim 5, wherein the PEG moieties have an average molecular weight greater than about 5000.

7. The composition of claim 1, wherein the functionalized single-wall carbon nanotubes comprise at least one tissue-targeting moiety selected from a group consisting of aptamers, antibodies, antibody fragments, saccharides, peptides, proteins, hormones, and receptor ligands.

8. The composition of claim 1, wherein the functionalized single-wall carbon nanotubes comprise at least one folate moiety.

9. The composition of claim 1, wherein the composition provides an extended in vivo release of paclitaxel;
   wherein the extended in vivo release comprises a greater in vivo residence time of paclitaxel compared to that of paclitaxel alone.

10. The composition of claim 1, wherein the composition provides intracellular delivery of paclitaxel.

11. A paclitaxel extended release formulation comprising:
   a solution of functionalized single-wall carbon nanotubes;
      wherein the functionalized single-wall carbon nanotubes are water-soluble;
      wherein the functionalized single-wall carbon nanotubes are covalently functionalized with a plurality of PEG moieties; and
      wherein the solution comprises water; and
   a quantity of paclitaxel, wherein the paclitaxel is non-covalently associated with the functionalized single-wall carbon nanotubes and sequestered from its surrounding environment by the non-covalent association with the functionalized single-wall carbon nanotubes.

12. The extended release formulation of claim 11, wherein the solution is a PBS buffer.

13. The extended release formulation of claim 11, wherein the PEG moieties have an average molecular weight greater than about 400.

14. The extended release formulation of claim 13, wherein the PEG moieties have an average molecular weight greater than about 2000.

15. The extended release formulation of claim 14, wherein the PEG moieties have an average molecular weight greater than about 5000.

16. The extended release formulation of claim 11, wherein the quantity of paclitaxel is at least 1 mg of paclitaxel per 1 mL of the solution.

17. The extended release formulation of claim 11, wherein an in vivo paclitaxel residence time is greater than that of paclitaxel alone.

18. The extended release formulation of claim 11, wherein the paclitaxel is delivered intracellularly.

\* \* \* \* \*